United States Patent [19]

Genet et al.

[11] Patent Number: 5,084,582

[45] Date of Patent: Jan. 28, 1992

[54] OXIDATION OF EPOXY ALCOHOLS INTO CARBOXILIC EPOXY ACIDS

[75] Inventors: Jean-Pierre Genet, Fontenay-aux Roses; Dominique Pons, Paris; Sylvain Juge, Orsay, all of France

[73] Assignee: Societe Nationale Elf Aquitaine, France

[21] Appl. No.: 635,524

[22] PCT Filed: Jun. 23, 1989

[86] PCT No.: PCT/FR89/00320

§ 371 Date: Jan. 18, 1991

§ 102(e) Date: Jan. 18, 1991

[87] PCT Pub. No.: WO90/00167

PCT Pub. Date: Jan. 11, 1990

[30] Foreign Application Priority Data

Jul. 1, 1988 [FR] France .............................. 88 08905

[51] Int. Cl.$^5$ ................. C07D 301/00; C07D 303/38; C07D 303/48
[52] U.S. Cl. ..................................... 549/513; 549/549
[58] Field of Search ................................ 549/513, 549

[56] References Cited

U.S. PATENT DOCUMENTS 4,007,217  2/1977  Kogure et al. ..................... 549/549

FOREIGN PATENT DOCUMENTS 2609032  7/1988  France ............................... 549/549

OTHER PUBLICATIONS

Journal of Organic Chemistry, vol. 46, No. 19, 9/11/81, Carlsen et al., "A Greatly Improved Procedure for Ruthenium Tetraoxide Catalyzed Oxidations of Organic Compounds".

Tetrahedron Letters, vol. 22, No. 18, 1981, Menger et al., "Synthetically Useful Oxidations at Solid Sodium Permanganate Surfaces".

*Primary Examiner*—C. Warren Ivy
*Assistant Examiner*—Raymond Covington
*Attorney, Agent, or Firm*—Ostrolenk, Faber, Gerb & Soffen

[57] ABSTRACT

The invention relates to a method of oxidizing epoxyalcohols, in a medium containing an organic solvent and water, by means of a solid oxidizing compound, in the presence of a catalyst based on a ruthenium salt. The proportion of water relative to that of organic solvent is sufficiently small for at least the major part of the oxidizing compound to remain in the solid state in the reaction medium, which is heterogeneous.

18 Claims, No Drawings

OXIDATION OF EPOXY ALCOHOLS INTO CARBOXILIC EPOXY ACIDS

The present invention relates to the preparation of epoxycarboxylic acids. It is based especially on the oxidation, in a liquid medium, of alcohols carrying an epoxy bridge. The method of this invention is particularly useful for obtaining very water-soluble epoxyacids of relatively low molecular weight, which are generally difficult to recover industrially from the aqueous medium. Especially epoxyacids having a $C_3$ to $C_{10}$ and particularly $C_3$ to $C_5$ aliphatic chain are favorably amenable to the method of the invention.

Epoxycarboxylic acids have a variety of industrial applications, especially for the synthesis of different derivatives of acids, esters or corresponding salts. Thus, for example, they are used for the synthesis of compounds of biological interest, such as amino acids, pheromones, antibiotics etc. In these fields, the invention brings a marked advantage in that it enables an epoxyacid to be obtained from an optically active alcohol without loss of the chirality desired for the remainder of the synthesis.

The invention enables the epoxyacids to be recovered easily and economically from the medium in which they were prepared. They are recovered by the evaporation of an organic solvent in which the acid prepared is present at the end of the preparation, said solvent being more volatile than this acid.

In the method according to the invention, which consists in oxidizing epoxyalcohols, in a medium containing an organic solvent and water, by means of an oxidizing compound, in the presence of a catalyst based on a ruthenium salt, the proportion of water relative to that of organic solvent is sufficiently small for at least the major part of the oxidizing agent to be in the solid state in the reaction medium, which is heterogeneous.

Depending on the nature of the alcohol to be oxidized, and especially on its miscibility with solvents, solvents which can be employed are ethers, hydrocarbons, halogenated hydrocarbons, nitriles or other organic liquids which are non-oxidizable under the operating conditions of the invention. Thus, for example, it is possible to operate in dioxane, tetrahydrofuran, toluene, octane, decane, dichloroethane, trichloroethylene, chloroform, carbon tetrachloride etc. Particularly useful solvents are those such as methylene chloride and acetonitrile. It is preferred to choose a solvent which is more volatile than the acid to be prepared.

Suitable oxidizing agents are various salts of the oxygenated anions of halogens, such as hypochlorites, hypobromites, chlorites, bromites, iodites, chlorates, bromates, iodates, perbromates or periodates of alkali metals and alkaline earth metals and, if appropriate, those of Zn, Al, Fe etc. Preferred oxidizing agents are hypochlorites and periodates of Na, K or Ca.

The catalysts employed in the method of the invention are Ru salts, in particular $RuCl_3$.

An important feature of the invention is that the proportion of water in the reaction medium does not exceed 20 mol of $H_2O$ per mol of alcohol to be oxidized, the volume of organic solvent being greater than that of water, preferably at least twice as much.

The preferred conditions in this method correspond to a proportion of $H_2O$ of 0.2 to 20 mol per mol of alcohol, preferably 0.5 to 5 and more particularly 1 to 2 mol. This is assured as long as the volume of solvent is adjusted to a value of about 5 to 250 times that of water, preferably 10 to 100 times.

In contrast to the information given in the prior art for a relatively high-molecular epoxyacid containing an aryl group, the highly water-soluble lower-molecular epoxycarboxylic acids cannot be extracted by the classical means from the reaction medium containing a greater or lesser proportion of water. Thus, in J. Org. Chem. 1981, 46, no. 19, top left of page 3938, under (1)[b], Carlsen, Katsuki, Martin and Sharpless report the oxidation of 4-phenyl-2,3-epoxybutan-1-ol in solution in acetonitrile, in the presence of 3 ml of water per mmol of this alcohol (i.e. 166 mol of $H_2O$/mol of alcohol), by means of 3 equivalents of sodium metaperiodate ($NaIO_4$), with 2.2 mol % of $RuCl_3.H_2O$ as catalyst, for 1 hour. The authors give proof for obtaining the corresponding carboxylic acid with a yield of 75% according to the reaction

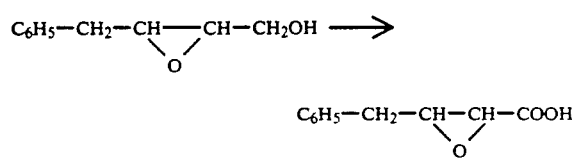

Now, the experiments culminating in the present invention have shown that, in practice, for the epoxyalcohols

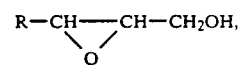

in which R is H or a $C_1$ to $C_7$ alkyl, especially H, $C_1$ or $C_2$, the acid formed can only be recovered by evaporation of the solvent, at the end of the reaction, if the proportion of $H_2O$ in the reaction medium is less than 20 mol of $H_2O$ per mol of alcohol to be oxidized, and preferably not more than 2 mol of $H_2O$ per mol of alcohol (as opposed to 166 mol in the afore-mentioned prior art).

According to an article by MENGER and LEE in TETRAHEDRON LETTERS, vol. 22, no. 18, pages 1655–1656, of 1981, alcohols can be oxidized to ketones by means of solid $NaMnO_4.H_2O$ in benzene; thus the reaction is carried out without liquid water and without a catalyst, i.e. under conditions very different from those of the present invention; it should moreover be noted that permanganate is a very much more expensive product than the oxygenated halogen compounds, in particular calcium hypochlorite, which can be employed in the present invention.

Finally, in the method of oxidizing epoxy-alcohols to epoxycarboxylic acids, in a medium containing an organic solvent and water, by means of a solid oxidizing compound, in the presence of a catalyst based on a ruthenium salt, the proportion of water relative to that of organic solvent is sufficiently small for at least the major part of the oxidizing compound to remain in the solid state in the reaction medium, which is heterogeneous, and the proportion of $H_2O$ in the reaction medium is from 0.2 to 20 mol per mol of epoxyalcohol.

The method is preferably carried out with 1.5 to 3 equivalents of oxidizing agent per alcohol group to be oxidized; thus it is particularly suitable to use 1.5 to 3 mol of $NaIO_4$ or 0.75 to 1.5 mol of $Ca(ClO)_2$ per —OH group, the oxidizing agent being introduced into the reaction mixture in the form of a fine powder. The amounts of oxidizing agent per unit of the total volume of solvent + water are preferably of the order of 0.5 to 2 equivalents per liter and especially of the order of 0.7 to 1.5 eq./l.

The catalyst of particular interest, $RuCl_3$, can advantageously be employed at a rate of 0.1 to 5% by weight of the reaction mixture.

The method of the invention can be carried out at various temperatures, especially from $-20°$ to $+80°$ C., preferably between 10° and 40° C. and in particular between 20° and 30° C.

It is recommended to monitor the operation and to stop it when the maximum conversion is reached. The optimum duration depends on various factors, especially the nature of the alcohol treated, the temperature and the excess of oxidizing salt; most frequently, at room temperature, the appropriate reaction times are from 1 to 16 hours and mainly from 2 to 12 hours.

In one particular embodiment of the invention, the yield is improved and the operating time can be shortened by the addition of a surface-active compound to the reaction medium. From about 0.1 to 1% by weight of surfactant, relative to the weight of the mixture, is generally sufficient. The surfactant is preferably selected from those which do not contain an alcohol group; suitable examples are compounds of the ether type, sulfates or sulfonates, such as polyoxyethylene fatty acid esters, especially polyoxyethylene laurate or stearate ("NONISOLS"), sodium dodecylsulfate ("SDS"), sodium alkanesulfonates (of petroleum: "PETRONATE HL"), sodium alkylarylsulfonates such as sodium octadecylbenzenesulfonate or sodium laurylbenzenesulfonate, etc.

The invention is illustrated by the non-limiting Examples whose results are reported below.

The procedure in these experiments consisted in dissolving an epoxyalcohol in the solvent methylene chloride, $CH_2Cl_2$, or acetonitrile, $CH_3CN$, adding 2.2 mol % of $RuCl_3.H_2O$ followed by a small amount of water and sodium periodate, $NaIO_4$, as a fine powder, or $Ca(ClO)_2$, and stirring the mixture continuously, at 25° C., for the indicated time. All the experiments were carried out on 10 to 12 mmol of epoxyalcohol and 10 to 20 ml of solvent, the other parameters being indicated in the Table of Results. The Table shows the % yield of carboxylic acid recovered, relative to the alcohol used. "$H_2O$" represents the number of mol of $H_2O$ per mol of alcohol used. "$H_2O$/solvent" denotes the volume of water relative to the volume of organic solvent.

EXAMPLES 1 TO 5

Oxidation of 2,3-epoxybutan-1-ol to 2,3-epoxybutyric acid

The reaction mixture consists in each case of 0.01 mol (0.88 g) of

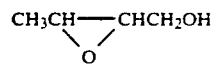

in 20 ml of $CCl_4$ to which 0.125 g of $RuCl_3.H_2O$ and 3 equivalents of sodium metaiodate, i.e. 0.03 mol of $NaIO_4$ (6.4 g), as a fine powder, have been added.

Different amounts of water are added to the mixtures, ranging from 30 ml in Example 1 to 0.3 ml in Example 5.

The operations are carried out by the procedure described above, at 25° C. The yield of epoxycarboxylic acid collected after evaporation of the solvent from the reaction mixture is determined.

The results are collated in the Table below.

| TABLE OF RESULTS | | | | |
|---|---|---|---|---|
| Example | Mol of $H_2O$/alcohol at the start | Volume of $H_2O$ solvent | Time in h | Yield of acid |
| 1 | 166 | 1.5 | 36 | 0 |
| 2 | 55 | 0.5 | " | 0 |
| 3 | 5.5 | 0.05 | " | very low |
| 4 | 2.44 | 0.025 | 24 | low |
| 5 | 1.46 | 0.015 | 6 | 75% |
| 5 after 1 h | 2.44 | 0.025 | — | " |

It follows that for a recovered yield of 75% of epoxybutyric acid, the initial proportion of water must not exceed 1.46 mol per mol of epoxybutyl alcohol.

EXAMPLE 6

The experiments of Examples 1 to 5 are repeated with acetonitrile, $CH_3CN$, in place of $CCl_4$ as the solvent. The same results are obtained.

EXAMPLE 7

The sodium metaperiodate in Example 5 is replaced with 1.5 equivalents of calcium hypochlorite, $Ca(ClO)_2$. After 5 hours at 25° C., the yield of epoxybutyric acid is 76%.

EXAMPLE 8

The technique of the preceding Examples is applied to the reaction

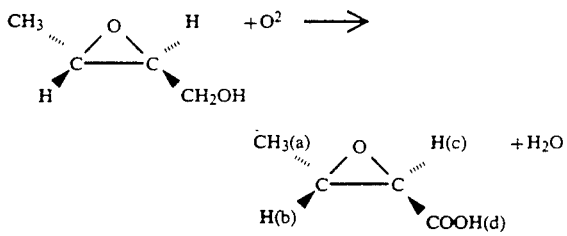

in which the chirality of the alcohol is wholly retained in the acid obtained.

The reaction was carried out by placing 11.35 ml of acetonitrile, 0.3 ml of water, 0.0113 mol of the epoxyalcohol indicated above and 0.0339 mol of $NaIO_4$ in a round-bottomed flask equipped with a magnetic stirrer, under an argon atmosphere. 2.2 mol % of $RuCl_3.H_2O$ were added to the mixture obtained. After stirring for one hour at 25° C., 0.2 ml of water was added. The mixture was then diluted with methylene chloride and filtered on Célite. After concentration by evaporation, the residue was diluted with ethyl ether and filtered again. The product obtained after evaporation of the solvents gave the following analysis:

| C | 47.1% | H | 5.6% |

|            |       |      |
|------------|-------|------|
| calculated | 47.0% | 5.9% |

$^1$H NMR 80 MHz (CDCl$_3$+TMS): H(a) 1.5 ppm (d, 3H); H(b-c) 3.4 ppm (m, 2H); H(d) 10.75 ppm (s, 1H).

The yield of this acid was 75%.

It should be noted that the initial amount of water in the mixture was 1.46 mol of H$_2$O per mol of alcohol used and that it increased to 2.44 mol when a further amount was added after one hour.

EXAMPLE 9

Following the procedure of Example 8, 2,3-epoxy-propan-1-ol,

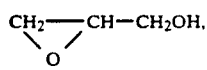

was oxidized with calcium hypochlorite to give epoxy-propionic acid,

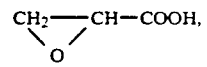

with a recovered yield of 77%.

What is claimed is:

1. A method of oxidizing epoxyalcohols to epoxycarboxylic acids, in a medium containing an organic solvent and water, by means of a solid oxidizing compound, in the presence of a catalyst based on a ruthenium salt, wherein the proportion of water relative to that of organic solvent is sufficiently small for at least the major part of the oxidizing compound to remain in the solid state in the reaction medium, which is heterogeneous, and wherein the proportion of H$_2$O in this medium is from 0.2 to 20 mol per mol of epoxyalcohol.

2. A method according to claim 1, wherein the proportion of water is from 0.5 to 5 mol per mol of epoxyalcohol.

3. A method according to claim 1, wherein the volume of organic solvent is 5 to 250 times that of water.

4. A method according to any one of claims 1, wherein the oxidizing compound is an alkali metal, alkaline earth metal, Zn, Al or Fe salt of an oxygenated anion of a halogen.

5. A method according to claim 4, wherein the oxidizing salt is a hypochlorite, hypobromite, hypoiodite, chlorite, bromite, iodite, chlorate, bromate or iodate.

6. A method according to claim 4, wherein the oxidizing salt is a hypochlorite or periodate of Na, K or Ca.

7. A method according to any one of claims 1, wherein the oxidation is carried out at a temperature of $-20°$ to $+80°$ C.

8. A method according to of claim 1, wherein the organic solvent is selected from ethers, hydrocarbons, halogenated hydrocarbons and nitriles which are non-oxidizable under the operating conditions and are preferably more volatile than the acid to be prepared.

9. A method according to claim 8, wherein the solvent is methylene chloride or acetonitrile.

10. A method according to claim 1, wherein a surface-active compound is added to the reaction medium.

11. A method according to claim 1, wherein a portion of water is added to the reaction medium after a reaction time of up to a few hours.

12. A method according to claim 1, wherein the proportion of water is from 1 to 2 mol per mol of epoxyalcohol.

13. Application of the method according to claim 1 to the preparation of C$_3$ to C$_{10}$ and in particular C$_3$ to C$_5$ aliphatic acids.

14. A method according to claim 3, wherein the volume or organic solvent is 10 to 100 times that of water.

15. A method according to claim 7, wherein the oxidation is carried out at a temperature between $+10°$ and $+40°$ C.

16. A method according to claim 15, wherein the oxidation is carried out between 20° and 30° C.

17. A method according to claim 2, wherein the volume of organic solvent is 10 to 100 times that of water.

18. A method according to claim 17, wherein the proportion of water is from 1 to 2 mol per mole of epoxyalcohol.

* * * * *